(12) United States Patent
Goldenberg

(10) Patent No.: US 6,319,500 B1
(45) Date of Patent: Nov. 20, 2001

(54) DETECTION AND TREATMENT OF INFECTIONS WITH IMMUNOCONJUGATES

(75) Inventor: M. David Goldenberg, Short Hills, NJ (US)

(73) Assignee: Immunomedics, Inc., Morris Plains, NJ (US)

( * ) Notice: Subject to any disclaimer, the term of this patent is extended or adjusted under 35 U.S.C. 154(b) by 0 days.

(21) Appl. No.: 08/158,782

(22) Filed: Dec. 1, 1993

Related U.S. Application Data

(62) Division of application No. 08/037,659, filed on Mar. 22, 1993, now Pat. No. 5,332,567, which is a continuation of application No. 07/840,591, filed on Feb. 18, 1992, now abandoned, which is a continuation of application No. 07/399,566, filed on Aug. 24, 1989, now abandoned.

(51) Int. Cl.[7] .................. A61K 39/395; A61K 39/40; A61K 39/42; A61K 39/44
(52) U.S. Cl. .................. 424/178.1; 424/179.1; 424/9.1; 424/184.1; 530/351; 530/387.1; 530/391.3; 530/391.5; 530/391.07
(58) Field of Search ............... 424/178.1, 1.48, 424/9, 179.1; 530/351, 387.1, 391.3, 391.5, 391.7

(56) References Cited

U.S. PATENT DOCUMENTS

| | | | |
|---|---|---|---|
| 4,671,958 | * | 6/1987 | Rodwell et al. ............ 424/85 |
| 4,824,659 | * | 4/1989 | Hawthorne ............... 424/1.1 |
| 4,835,259 | * | 5/1989 | Reese ..................... 530/395 |
| 4,867,973 | * | 9/1989 | Goers et al. ............ 424/85.91 |
| 4,925,648 | * | 5/1990 | Hansen et al. ........... 424/1.1 |
| 5,120,525 | * | 6/1992 | Goldenberg ............ 424/1.1 |
| 5,332,567 | * | 7/1994 | Goldenberg ........... 424/1.49 |

FOREIGN PATENT DOCUMENTS

8809181 * 1/1988 (WO).
88/09181   12/1988 (WO).

OTHER PUBLICATIONS

Holder, A.A. et al., J. Exp. Med., 156:1528–1538, Nov. 1982.*
Goldenberg, National Institutes of Health grant, 1990, 5R35Ca39841–06 (1984), Federal Research in Progress data base.
Vallera, "Immunotoxius for ex vivo bone marrow purging in human bone marrow transplantation", A. Frankel, Ed., Kluwer Pub., 1988, p. 515–535.
Bjorn, "Immunotoxins: Selection of cell–surface antigens and their corresponding monoclonal antibodies", A. Frankel, Ed., Kluwer Pub., 1988, p. 255–277.
Costa, et al., "Immunoglobulin binding to herpes virus induced Fc receptors inhibits virus growth", Nature 269:251–252, 1977.
Torpier, et al, "Receptor for IgG(Fc) and human β–microglobulin on *S. mansoni* schistosomula", Nature, 278:472–449, Mar. 1979.
Foung, "Human Monoclonal antibodies of Human Cytomegalovirus", Journal of Infectious Diseases, vol. 159, No. 3, (Mar. 1989), p. 436–443.
Brennan, M. et al., Science, 229:81–83, Jul. 5, 1985.*

* cited by examiner

*Primary Examiner*—James Housel
*Assistant Examiner*—Brett Nelson
(74) *Attorney, Agent, or Firm*—Foley & Lardner

(57) ABSTRACT

A method of targeting a diagnostic or therapeutic agent to a focus of infection comprises injecting a patient infected with a pathogen parenterally with an antibody conjugate which specifically binds to an accessible epitope of the pathogen or of a pathogen-associated antigen accreted at the focus of infection, the antibody conjugate further comprising a bound diagnostic or therapeutic agent for detecting, imaging or treating the infection. Polyspecific composite conjugates enhance the efficacy of the method, which is especially useful for treating infections that are refractory towards systemic chemotherapy.

31 Claims, No Drawings

DETECTION AND TREATMENT OF INFECTIONS WITH IMMUNOCONJUGATES

This application is a division of application Ser. No. 08/037,659, filed Mar. 22, 1993, now U.S. Pat. No. 5,322,567 which is a continuation of Ser. No. 07/840,591, filed Feb. 18, 1992, now abandoned which is a continuation of Ser. No. 07/399,566, now abandoned; filed Aug. 24, 1989.

BACKGROUND OF THE INVENTION

This invention relates to reagents and methods for targeting a diagnostic and/or therapeutic agent to a focus of pathogenic infection by using as the targeting vehicle an antibody conjugate that specifically binds to one or more accessible epitopes of the pathogen or of a pathogen-associated antigen.

Drug therapy against pathogens is conventionally effected by means of systemic administration the drug in order to achieve a blood level which toxic to the pathogen wherever it is harbored in the body. Thus, a certain blood level is necessary in order to provide the proper concentration of the drug at the site of infection. This requires high doses and often does not achieve the desired toxicity without resulting in unacceptably adverse side-effects to the patient, since many of these drugs have general cytotoxic properties.

The development and description of murine monoclonal antibodies (MAbs) against infectious organisms has been the subject of a number of reviews (eg., M. C. Harris et al., Indian J. Pediatr., 54:481–488, 1987; S. Cohen, Brit. Med. Bull., 40:291–296, 1984; R. A. Polin, Eur J. Clin. Microbiol., 3:387–398, 1984; R. C. Nowinski et al., Science, 219:637–644, 1983; Part V, Monoclonal Antibodies to Microorganisms, Chapters 17–20, inclusive, In: R. H. Kennett et al., (eds.), *Monoclonal Antibodies. Hybridomas: A New Dimension in Biological Analyses*, New York and London, Plenum Press, 1980, pp. 295–362). These papers, and others in this area, have been concerned with the use of such monoclonal antibody reagents for improved diagnostic tests for the infectious microorganisms, including bacteria, viruses, protozoa and helminths.

It has been proposed that these MAbs can be used as such for both the diagnosis and therapy of certain bacterial diseases, such as group B streptococcal infections (Harris, cited above), but exclusively as diagnostic agents in viral diseases (Harris, cited above). In the case of group B streptococcal infections, MAbs were used in rodents to treat the infection, and it was found in these limited trials that only when the MAbs were infused early after infection was an effect achieved; at 6 hours or later, no survival of the animal occurred (Christensen et al., Pediatric Res., 18:1093–1096, 1984). In the case of malarial parasites, it has been shown that the Fab fragments of a monoclonal antibody directed against the surface coat of malaria sporozoites is active in protecting mice against malarial infection, indicating that it blocks attachment of sporozoites to host receptor cells (P. Potocnjak et al., J. Exp. Med., 151:1504–1513, 1980). This further indicates, since it is achieved by the immunoglobulin molecule lacking the Fc portion, that the protective antibody action is independent of complement or cells.

These animal experiments indicate that early infections can be affected by the use of organism-specific MAbs in well-controlled laboratory experiments involving certain bacteria and parasites. Despite these reports a number of years ago, MAbs have not been shown to have a therapeutic role in infectious diseases in humans. One major reason has been that such MAbs exert a protective action only in specific, usually early stages of infection, being less able to interact with the infectious organisms when they have disseminated into tissue reservoirs that are less accessible to interaction with the injected MAbs. Use of such MAbs to form therapeutic conjugates is not suggested by the references.

A need therefore exists for a method of targeting a diagnostic agent, e.g., an imaging agent, or a therapy agent, e.g., a drug or radioisotope, to a focus of infection with higher efficiency and an enhanced therapeutic index to permit more effective diagnosis and/or treatment of the infection.

OBJECTS OF THE INVENTION

One object of the present invention is to provide an effective and selective method of targeting a focus of infection.

Another object of the invention is to provide diagnostic and therapeutic agents with high specificity for foci of infection.

Another object of the invention is to provide an alternative or adjunct to chemotherapy for treatment of certain microbial and parasitic infections that are not amenable or relatively unresponsive to chemotherapy and which cause debilitating or life-threatening illness.

Another object of the invention is to improve the therapeutic index of a chemotherapeutic agent and/or radiopharmaceutical.

Other objects of the present invention will become more apparent to those of ordinary skill in the art in light of the following discussion.

SUMMARY OF THE INVENTION

These and other objects of the present invention are achieved by providing a method of targeting a diagnostic or therapeutic agent to a focus of infection, which comprises injecting a patient infected with a pathogen parenterally with an antibody conjugate which specifically binds to an accessible epitope of said pathogen or of a pathogen-associated antigen accreted at said focus of infection, said antibody conjugate further comprising a bound diagnostic or therapeutic agent for detecting, imaging or treating said infection.

The invention further provides polyspecific or monospecific antibody conjugates for targeting foci of infection, comprising an immunoreactive component including at least one substantially monospecific antibody or antibody fragment, conjugated to at least one diagnostic or therapeutic agent, wherein the antibody or antibody fragment specifically binds to an accessible epitope of the pathogen or of a pathogen-associated antigen. These can be provided in the form of sterile injectable preparations and kits for use in practicing the foregoing method.

DETAILED DESCRIPTION

Antimicrobial agents are conventionally classified into four main groups, based upon their affecting (1) bacterial cell-wall synthesis, (2) the cytoplasmic membrane, (3) protein synthesis, and (4) nucleic acid synthesis, and often each of these groups can be subdivided into several classes. Reviews of antimicrobial chemotherapy can be found in the chapter by M. P. E. Slack (In: Oxford Textbook of Medicine, Second Ed., Vol. I, edited by D. J. Weatherall, J. G. G. Lidingham, and D. A. Warrell, pp. 5.35–5.53; Oxford University Press, Oxford/Melbourne/New York, 1987) and in Section XII, Chemotherapy of Microbial Diseases (In: Goodman and Gilman's The Pharmacological Basis of Therapeutics, 6th Ed., Goodman et al., Eds., pp. 1080–1248; Macmillan Publishing Co., New York, 1980).

As indicated in these texts, some antimicrobial agents are selective in their toxicity, since they kill or inhibit the microorganism at concentrations that are tolerated by the host (i.e., the drug acts on microbial structures or biosynthetic pathways that differ from those of the host's cells). Other agents are only capable of temporarily inhibiting the growth of the microbe, which may resume growth when the inhibitor is removed. Often, the ability to kill or inhibit a microbe or parasite is a function of the agent's concentration in the body and its fluids.

Whereas these principles and the available antimicrobial drugs have been successful for the treatment of many infections, particularly bacterial infections, other infections have been resistant or relatively unresponsive to systemic chemotherapy, e.g., viral infections and certain fungal, protozoan and parasitic infections.

As used herein, "microbe" denotes virus, bacteria, rickettsia, mycoplasma, protozoa and fungi, while "pathogen" denotes both microbes and infectious multicellular invertebrates, e.g., helminths, spirochetes and the like.

Virus can infect host cells and "hide" from circulating systemic drugs. Even when viral proliferation is active and the virus is released from host cells, systemic agents can be insufficiently potent at levels which are tolerated by the patient.

Similarly, a number of fungal, protozoan and parasitic infections have been resistant to systemic drug therapy, at least in part because an effective antipathogenic dose of a drug has been above the level which is tolerated by the patient or because the infection was difficultly accessible to conventional systemic routes of drug administration.

The present invention resolves many of the problems involved in the treatment of infections that are refractive to conventional drug therapy by using very specific antibodies made against microbial or parasitic antigens in order to target an effective radionuclide and/or chemical agent to foci of infection, thereby selectively killing the pathogen. A targeted drug can have enhanced effectiveness due to significantly increased concentration at the target site relative to the rest of the body. The targeting antibody is able to bind to an accessible epitope of the pathogen or to antigens shed by the pathogen or resulting from its fragmentation and/or destruction, and which accrete at a focus of infection The epitope can be on the surface of the pathogen or antigen or at an accessible locus in the pathogen. The therapeutic component of the conjugate is thereby localized at the target site with higher efficiency and an enhanced target to non-target ratio.

Targeting is also effective for diagnostic agents, especially agents for scintigraphic imaging or magnetic resonance imaging (MRI) of sites of infection. This is helpful to the treating physician for evaluation of the patient's level and stage of infection and for designing and monitoring treatment protocols.

The antibody component of the conjugate can be a single monospecific antibody reacting with one epitope of the pathogen or its antigen. In such a case, it is preferable for the antibody to bind to an epitope that is different and separate from epitopes to which the patient's own antibodies bind. This will avoid the problem of blocking due to saturation of the pathogen or its antigen with native antibodies, and consequent inhibition of targeting.

Alternatively, the antibody component can be polyspecific, i.e., it can include a plurality of antibodies that bind to a plurality of epitopes on the pathogen or its antigen. The polyspecific antibody component can be a polyclonal antiserum, preferably affinity purified, from an animal which has been challenged with an immunogenic form of the pathogen or its antigen and stimulated to produce a plurality of specific antibodies against the pathogen or its antigen. Another alternative is to use an "engineered polyclonal" mixture, which is a mixture of monoclonal antibodies with a defined range of epitopic specificities.

In both types of polyclonal mixtures, it can be advantageous to chemically link polyspecific antibodies together to form a single polyspecific molecule capable of binding to any of several epitopes. Conjugation of such a polyspecific targeting molecule with a diagnostic or therapeutic agent increases the likelihood that the agent will reach the site of infection, thereby increasing the target to non-target ratio and the efficacity of the vehicle. One way of effecting such a linkage is to make bivalent $F(ab')_2$ hybrid fragments by mixing two different $F(ab')_2$ fragments produced, e.g., by pepsin digestion of two different antibodies, reductive cleavage to form a mixture of Fab' fragments, followed by oxidative reformation of the disulfide linkages to produce a mixture of $F(ab')_2$ fragments including hybrid fragments containing a Fab' portion specific to each of the original antigens. Methods of preparing such hybrid antibody fragments are disclosed in Feteanu, "Labeled Antibodies in Biology and Medicine" pages 321–323 (McGraw-Hill Int. Bk. Co., New York et al, 1978); Nisonoff et al, Arch Biochem. Biophys., 93, 470 (1961); and Hammerling et al, J. Exp. Med., 128, 1461 (1968); and in U.S. Pat. No. 4,331,647.

Other methods are known in the art to make bivalent fragments that are entirely heterospecific, e.g., use of bifunctional linkers to join cleaved fragments. Recombinant molecules are known that incorporate the light and heavy chains of an antibody, e.g., according to the method of Boss et al., U.S. Pat. No. 4,816,397. Analogous methods of producing recombinant or synthetic binding molecules having the characteristics of antibodies are included in the invention. More than two different mono-specific antibodies or antibody fragments can be linked using various linkers known in the art.

The immunological profile of the substantially monospecific, preferably monoclonal, antibodies used to make the polyspecific conjugates of the present invention can be adjusted to ensure optimal binding to the pathogen or its antigens by mixing the antibody specificities for different antigens and their epitopes in particular cases of infections, as well as of binding constants for the target epitopes, so as to fine tune the selectivity and targeting efficiency of the reagent according to the invention.

An imaging reagent according to the invention can comprise bispecific, trispecific or, more generally, polyspecific antibody/fragment conjugates, further comprising an imaging radioisotope or paramagnetic species.

The antibody component of the conjugate can include whole antibodies, antibody fragments, or subfragments. Use of the term "antibody" herein will be understood to embrace whole antibodies, antibody fragments and subfragments and thus to be equivalent to the term "antibody/fragment" which is used interchangeably therefor in this discussion, unless otherwise noted. Antibodies can be whole immunoglobulin (IgG) of any class, e.g., IgG, IgM, IgA, IgD, IgE, chimeric antibodies or hybrid antibodies with dual or multiple antigen or epitope specifities, or fragments, e.g., F(ab')$_2$, Fab', Fab and the like, including hybrid fragments, and additionally includes any immunoglobulin or any natural, synthetic or genetically engineered protein that acts like an antibody by binding to a specific antigen to form a complex.

Antibodies can include antiserum preparations from a variety of commonly used animals, e.g., goats, primates, donkeys, swine, rabbits, horses, hens, guinea pigs, rats or mice, and even human antisera after appropriate selection and purification. The animal antisera are raised by inoculating the animals with an immunogenic form of the pathogen or its antigen, by conventional methods, bleeding the animals and recovering serum or an immunoglobulin-containing serum fraction.

The antiserum is preferably affinity-purified by conventional procedures, e.g., by binding antigen to a chromatographic column packing, e.g., Sephadex, passing the antiserum through the column, thereby retaining specific antibodies and separating out other immunoglobulins and contaminants, and then recovering purified antibodies by elution with a chaotropic agent, optionally followed by further purification, e.g., by passage through a column of bound blood group antigens or other non-pathogen species. This procedure may be preferred when isolating the desired antibodies from the serum of patients having developed an antibody titer against the pathogen in question, thus assuring the retention of antibodies that are capable of binding to exposed epitopes.

Hybridoma-derived monoclonal antibodies (human, monkey, rat, mouse, or the like) are also suitable for use in the present invention and have the advantage of high specificity. They are readily prepared by what are now generally considered conventional procedures for immunization of mammals with an immunogenic antigen preparation, fusion of immune lymph or spleen cells, with an immortal myeloma cell line, and isolation of specific hybridoma clones. More unconventional methods of preparing monoclonal antibodies are not excluded, such as interspecies fusions and genetic engineering manipulations of hypervariable regions, since it is primarily the antigen specificity of the antibodies that affects their utility in the present invention. Human lymphocytes can be fused with a human myeloma cell line to produce antibodies with particular specificities, preferably to epitopes which are not masked by circulating antibodies to the major antigenic sites on the pathogen.

The present invention also envisions the use of antigen-specific fragments to create the poly-specific antibody conjugate. Antibody fragments can be made by pepsin or papain digestion of whole immunoglobulins by conventional methods. It is known that antibody fragments may be produced by enzymatic cleavage of antibodies with pepsin to provide a 5S fragment denoted F(ab')$_2$. This fragment can be further cleaved using a thiol reducing agent, and optionally a blocking group for the sulfhydryl groups resulting from cleavage of disulfide linkages; to produce 3.5S Fab' monovalent fragments. Alternatively, an enzymatic cleavage using pepain produces two monovalent Fab fragments and an Fc fragment directly. These methods are described, inter alia, by Goldenberg, in U.S. Pat. Nos. 4,036,945 and 4,331,647 and references contained therein, which patents are incorporated herein in their entireties by reference, and in Nisonoff et al, Arch. Biochem. Biophys., 89, 230 (1960); Porter, Biochem. J., 73, 119 (1959); and Edelman et al, in "Methods in Immunology and Immunochemistry", Vol. 1, 422 (Acad. Press, 1967), and are conventional in the art.

Other methods of cleaving antibodies, such as separation of heavy chains to form monovalent light-heavy chain fragments, further cleavage of fragments, or other enzymatic, chemical or genetic techniques may also be used, so long as the fragments retain specificity to the pathogen or antigen against which their parent antibodies are raised.

Antibodies to virus or viral antigens may be made by inoculating a host with crude or purified, live, attenuated or killed virus or with antigens shed by virus, e.g., coat protein, portions thereof, or fragments resulting from destruction of virus. Monoclonal antibodies may be made by immunizing mice or other mammalian species with the virus or viral antigens, isolating splenocytes from the immunized host and fusing them with a suitable myeloma cell line using somatic cell hybridization techniques to produce hybridomas that produce antiviral antibodies. These hybridomas may be isolated, subcloned and cultivated to produce monoclonal antibodies. The hybridoma derived monoclonal antibodies to viral antigens are typically of murine or rat origin and typically are IgGs or IgMs, although suitable antibodies for use in preparing conjugates according to the invention are not intended to be limited as regards species or Ig class.

In general, antibodies can usually be raised to most antigens, using the many conventional techniques now well known in the art. Thus, antibodies that specifically bind to other microbial and parasitic antigens, either on the organism itself or on fragments or excreted or accreted antigens can be raised by adapting the foregoing methodology in ways that are now conventional in the art. Any antibody that binds to a pathogen or its antigen which is found in sufficient concentration at a focus of infection in the body of a mammal can be used to make the targeting conjugate for use in the present invention.

A wide variety of monoclonal antibodies against infectious disease agents have been developed, and are summarized in a review by Polin, in Eur. J. Clin. Microbiol., 3(5):387–398, 1984, showing ready availability. However, the principal interest in such antibodies in the past has been their incorporation into in vitro diagnostic assays. A few unconjugated antibodies have been tried as therapeutic gents in animal models, but with only limited success.

The value of conjugating such antibodies with radioisotopes and/or drugs or toxins to achieve targeted detection, imaging and therapy of infection has not been appreciated, and the efficacy of such agents could not be predicted from such prior disclosures.

Among the monoclonal antibodies (MAbs) against pathogens and their antigens cited by Polin, supra, are:
Anti-bacterial Mabs
*Streptococcus agalactiae*
*Legionella pneumophilia*
*Streptococcus pyogenes*
*Escherichia coli*
*Neisseria gonorrhosae*
*Neisseria meningitidis*
Pneumococcus
Hemophilis influenzae B
*Treponema pallidum*
Lyme disease spirochetes
*Pseudomonas aeruginosa*
*Mycobacterium leprae*
*Brucella abortus*
*Mycobacterium tuberculosis*
Tetanus toxin
Anti-viral MAbs
Rabies virus
Influenza virus
Cytomegalovirus Herpes simplex I and II
Human serum parvo-like virus
Respiratory syncytial virus
Varicella-Zoster virus
Hepatitis B virus
Measles virus
Adenovirus
Human T-cell leukemia viruses
Epstein-Barr virus
Murine leukiemia virus *
Mumps virus
Vesicular stomatitis virus
Sindbis virus
Lymphocytic choriomeningitis virus
Wart virus
Blue tongue virus
Sendai virus
Feline leukemia virus *
Reo virus
Polio virus
Simian virus 40 *
Mouse mammary tumor virus *
Dengue virus
Rubella virus
　　* Animal virus
Anti-protozoan MAbs
*Plasmodium falciparum*
*Plasmodium vivax*
*Toxoplasma gondii*
*Trypanosoma rangeli*
*Trypanosoma cruzi*
*Trypanosoma rhodesiensei*
*Trypanosoma brucei*
*Schistosoma mansoni*
*Schistosoma japanicum*
*Babesia bovis*
*Elmeria tenella*
*Onchocerca volvulus*
*Leishmania tropica*
*Trichinella spiralis*
*Theileria parva*
*Taenia hydatigena*
*Taenia ovis*
*Taenia saginata*
*Echinococcus granulosus*
*Mesocestoides corti*
Antimycoplasmal MAbs
*Mycoplasma arthritidis*
*M. hyorhinis*
*M. orale*
*M. arginini*
*Acholeplasma laidlawii*
*M. salivarium*
*M. pneumoniae*

Additional examples of MAbs generated against infectious microorganisms that have been described in the literature are noted below.

MAbs against malaria parasites can be directed against the sporozoite, merozoite, schizont and gametocyte stages. Monoclonal antibodies have been generated against sporozoites (circumsporozoite antigen), and have been shown to neutralize sporozoites in vitro and in rodents (N. Yoshida et al., Science 207:71–73, 1980).

Several groups have developed MAbs to *T. gondii*, the protozoan parasite involved in toxoplasmosis (Kasper et al., J. Immunol. 129:1694–1699, 1982; Id., 130:2407–2412, 1983).

MAbs have been developed against schistosomular surface antigens and have been found to act against schistosomulae in vivo or in vitro (Simpson et al. Parasitology, 83:163–177, 1981; Smith et al., Parasitology, 84:83–91, 1982; Gryzch et al., J. Immunol., 129:2739–2743, 1982; Zodda et al., J. Immunol. 129:2326–2328, 1982; Dissous et al., J. Immunol., 129:2232–2234, 1982).

*Trypanosoma cruzi* is the causative agent of Chagas' disease, and is transmitted by blood-sucking reduviid insects. A MAb has been generated that specifically inhibits the differentiation of one form of the parasite to another (epimastigote to trypomastigote stage) in vitro, and which reacts with a cell-surface glycoprotein; however, this antigen is absent from the mammalian (bloodstream) forms of the parasite (Sher et al., Nature, 300:639–640, 1982).

Suitable MAbs have been developed against most of the microorganisms (bacteria, viruses, protozoa, helminths) responsible for the majority of infections in humans, and many have been used previously for in vitro diagnostic purposes. These antibodies, and newer MAbs that can be generated by conventional methods for further improvement of targeting by use of MAb combinations, are appropriate for in vivo use as imaging and therapy reagents when they are conjugated with suitable radionuclides and drugs.

It is generally desirable to use antibodies having a relatively high immunoreactivity, i.e., a binding constant of at least about $10^5$/mole, preferably at least about $10^7$/mole, and high immunospecificity, i.e., at least about 40%, preferably at least about 60%, more preferably at least about 70–95% for pathogen antigens.

However, it may be preferable for certain applications, e.g., for imaging, to use antibodies having a somewhat lower binding constant in the present invention. Antibodies with high binding constants are likely to bind tightly not only to pathogens and their antigens at the site of infection, but also to such pathogens and/or antigens present in the circulatory system. On the other hand, antibodies with a lower binding constant will tend to accrete mainly at concentrated pathogen/antigen foci by virtue of a type of mass action effect. This will reduce premature clearance and nontarget accretion of the imaging label and thus increase the effective amount for targeting the focus of infection.

Antibody conjugates for imaging can be prepared by a variety of conventional procedures, ranging from simple glutaraldehyde linkage to more elegant and specific linkages between functional groups. The antibodies and/or antibody fragments are preferably covalently bound to one another, directly or through a short or long linker moiety, through one or more functional groups on the antibody/fragment, e.g., amine, carboxyl, phenyl, thiol or hydroxyl groups. Various conventional linkers in addition to glutaraldehyde can be used, e.g., diisiocyanates, diisothiocyanates, bis (hydroxysuccinimide) esters, carbodiimides, maleimide-hydroxysuccinimide esters and the like.

A simple method is to mix the antibodies/fragments in the presence of glutaraldehyde to form an antibody composite. The initial Schiff base linkages can be stabilized, e.g., by borohydride reduction to secondary amines. This method is conventionally used to prepare other conjugates of proteins, e.g., peroxidase-antibody conjugates for immunohistochemical uses or for immunoassays. A diisothiocyanate or a carbodiimide can be used in place of glutaraldehyde as a non-site-specific linker.

Bispecific antibodies can be made by a variety of conventional methods, e.g., disulfide cleavage and reformation of mixtures of whole IgG or, preferably F(ab')$_2$ fragments, fusions of more than one clone to form polyomas that produce immunoglobulins having more than one specificity, and by genetic engineering. The bispecific antibodies can bind to one or more viral epitopes. Bispecific ("hybrid") antibody fragments have been prepared by oxidative linkage of Fab' fragments resulting from reductive cleavage of different antibodies. A portion of these will contain fragments specific to both of the antigens to which the original antibodies were raised.

More selective linkage can be achieved by using a heterobifunctional linker such as a maleimide-hydroxysuccinimide ester. Reaction of the latter with an antibody/fragment will derivatize amine groups on the antibody/fragment, and the derivative can then be reacted with, e.g., an antibody Fab fragment with free sulfhydryl groups (or a larger fragment or intact immunoglobulin with sulfhydryl groups appended thereto by, e.g., Traut's Reagent). Such a linker is less likely to crosslink groups in the same antibody and improves the selectivity of the linkage.

It is advantageous to link the antibodies/fragments at sites remote from the antigen binding sites. This can be accomplished by, e.g., linkage to cleaved interchain sulfhydryl groups, as noted above. Another method involves reacting an antibody whose carbohydrate portion has been oxidized with another antibody which has at least one free amine function. This results in an initial Schiff base (imine) linkage, which is preferably stabilized by reduction to a secondary amine, e.g., by borohydride reduction, to form the final composite. Such site-specific linkages are disclosed, for small molecules or polypeptides or for solid phase polymer supports, in U.S. Pat. No. 4,671,958 and for larger addends in U.S. Pat. No. 4,699,784.

Similar reactions can be used to bind a plurality of antibodies and/or antibody fragments, e.g., Fab or F(ab')$_2$ fragments, to one another to form polyspecific conjugates or conjugates with more than one epitopic specificity for a pathogen or its antigen to increase its binding affinity or efficiency to the target site. Bispecific conjugates can be linked to an antibody/fragment specific to a third, fourth or further epitope using, e.g., a heterobifunctional maleimide-hydroxysuccinimide ester linker to derivatize an amine group, followed by reaction of the derivative with a fragment having a free sulfhydryl group, optionally introduced with a reagent such as 2-iminothiolane. Alternative linkage modes will be readily apparent to the ordinary skilled artisan based on the disclosures for bispecific composite formation, and will require only minor variation and adaptation of such methods.

The antibody component of the conjugate can be labeled with or conjugated or adapted for conjugation to, a radioisotope for scintigraphic imaging or a magnetic resonance image enhancing agent, for use as a diagnostic imaging agent. Any conventional method of radiolabeling which is suitable for labeling proteins for in vivo use will be generally suitable for labeling the composite. This can be achieved by direct labeling with, e.g., a radioisotope of a halogen or a metal ion, using conventional techniques or more sophisticated methodologies, or by attaching a chelator for a radiometal or paramagnetic ion. Such chelators and their modes of attachment to antibodies are well known to the ordinary skilled artisan and are disclosed inter alia in, e.g., Childs et al, J. Nuc. Med., 26:293 (1985); and in Goldenberg U.S. Pat. Nos. 4,331,647, 4,348,376, 4,361,544, 4,468,457, 4,444,744, and 4,624,846. Typical are derivatives of ethylenediaminetetraacetic acid (EDTA) and diethylenetriaminepentaacetic acid (DTPA). These typically have groups on the side chain by which the chelator can be attached to an antibody. Alternatively, carboxyl or amine groups on a chelator can be activated and then coupled to an antibody by well known methods. For example, deferoxamine, which is a chelator for Ga-67, has a free amine group that can be activated with a suitable linker to contain an activated carboxyl, isothiocyanate or like group, and then coupled to amines on an antibody.

The chelator may be bound to the antibody, directly or through a short or long chain linker moiety, through one or more functional groups on the antibody, e.g., amine, carboxyl, phenyl, thiol or hydroxyl groups. Various conventional linkers can be used, e.g., diisocyanates, diisothiocyanates, carbodiimides, bis-hydroxysuccinimide esters, maleimide-hydroxysuccinimide esters, glutaraldehyde and the like, preferably a selective sequential linker such as the anhydride-isothiocyante linker disclosed in U.S. Pat. No. 4,680,338.

Labeling with either Iodine-131 (I-131) or Iodine-123 (1-123), is readily effected using an oxidative procedure wherein a mixture of radioactive potassium or sodium iodide and the antibody is treated with chloramine-T, e.g., as reported by Greenwood et al, Biochem. J., 89, 114 (1963) and modified by McConahey et al, Int. Arch. Allergy Appl. Immunol., 29, 185 (1969). This results in direct substitution of iodine atoms for hydrogen atoms on the antibody molecule, presumable on tyrosine residues, possibly also on tryptophan and even on phenylalanine residues, depending on the proportions of reagents and the reaction conditions. Alternatively, lactoperoxidase iodination may be used as described by Feteanu, supra, page 303, and references cited therein.

Some more advanced methods of labeling are disclosed in pending applications U.S. Ser. Nos. 742,436 (Jun. 7, 1998), 084,544 (Aug. 12, 1987), and 176,421 (Apr. 1, 1988). The disclosures of all of the foregoing patents and applications are incorporated herein in their entireties by reference. A wide range of labeling techniques are disclosed in Feteanu, "Labeled Antibodies in Biology and Medicine", pages 214–309 (McGraw-Hill Int. Book Co., New York et al, 1978). The introduction of various metal radioisotopes may be accomplished according to the procedures of Wagner et al, J. Nucl. Med., 20,428 (1979); Sundberg et al, J. Med. Chem., 17, 1304 (1974); and Saha et al. J. Nucl. Med., 6, 542 (1976). The foregoing are merely illustrative of the many methods of radiolabeling proteins known to the art.

Examples of compounds useful for MRI image enhancement include paramagnetic ions, e.g., Gd(III), Eu(III), Dy(III), Pr(III), Pa(IV), Mn(II), Cr(III), Co(III), Fe(III), Cu(II), Ni(II), Ti(III), and V(IV) ions, or radicals, e.g., nitroxides, and these would be conjugated to a substrate bearing paramagnetic ion chelators or exposed chelating functional groups, e.g., SH, NH$_2$, COOH, for the ions, or linkers for the radical addends. The MRI enhancing agent must be present in sufficient amounts to enable detection by an external camera, using magnetic field strengths which are reasonably attainable and compatible with patient safety and instrumental design. The requirements for such agents are well known in the art for those agents which have their effect upon water molecules in the medium, and are disclosed, inter alia, in, e.g., Pykett, Scientific American, 246:78 (1982); and Runge et al., Am. J. Radiol, 141:1209 (1987).

It is well understood that many of the same methods for introducing metals, directly or in the form of chelates, into antibodies will be suitable for introduction of MRI agents into the antibody conjugates of the invention to form imaging agents for infections. MRI agents advantageously have a large number of paramagnetic ions or radicals for enhanced imaging. One method for introducing a plurality of such ions is to load a carrier polymer with chelates and link the carrier to the antibody composite, preferably site-specifically at a site remote from the antigen binding sites of the conjugate. This has the advantage that larger numbers of chelators can be attached to the antibody at fewer sites on the antibody itself, so that immunoreactivity is not as seriously compromised. Examples of polymers that are useful for loading the antibody with chelator include, e.g., polyols, polysaccharides, polypeptides and the like, such as those disclosed in, e.g., U.S. Pat. No. 4,699,784 (Shih et al) and U.S. Pat. No. 4,046,722 (Rowland).

One type of polysaccharide is dextran. The chelator can be functionalized to contain reactive groups towards the dextran hydroxyls, e.g., anhydrides, isocyanates or isothiocyanates and the like. Alternatively, dextran can be derivatized in a number of ways, e.g., by conversion to an aminodextran. It will be appreciated that similar methods will be useful for loading a plurality of drug molecules on an antibody or antibody conjugate, as will be discussed more fully hereinafter.

The process for preparing an antibody conjugate with an aminodextran (AD) carrier normally starts with a dextran polymer, advantageously a dextran of average molecular weight (MW) of about 10,000–100,000, preferably about 10,000–40,000, and more preferably about 15,000. The dextran is then reacted with an oxidizing agent to effect a controlled oxidation of a portion of its carbohydrate rings to generate aldehyde groups. The oxidation is conveniently effected with glycolytic chemical reagents, e.g., $NaIO_4$, according to conventional procedures.

It is convenient to adjust the amount of oxidizing agent so that about 50–150, preferably 100 aldehyde groups are generated, for a dextran of MW of about 40,000, with about the same proportion of aldehyde groups for other MW dextrans. A larger number of aldehyde groups, and subsequent amine groups, is less advantageous because the polymer then behaves more like polylysine. A lower number results in less desirable loading of the chelator or boron addend, which may be disadvantageous.

The oxidized dextran is then reacted with a polyamine, preferably a diamine, and more preferably a mono- or poly-hydroxy diamine. Suitable amines include, e.g., ethylenediamine, propylenediamine or similar polymethylendadiamines, diethylenetriamine or like polyamines, 1,3-diamino-2-hydroxypropane or otherwise like hydroxylated diamines or polyamines, and the like. An excess of the amine relative to the aldehyde groups can be used, to insure substantially complete conversion of the aldehyde functions to Schiff base (imine) groups.

Reductive stabilization of the resultant intermediate is effected by reacting the Schiff base intermediate with a reducing agent, e.g., $NaBH_4$, $NaBH_3CN$, or the like. An excess of the reducing agent is used to assure substantially complete reduction of the imine groups to secondary amine groups, and reduction of any unreacted aldehyde groups to hydroxyl groups. The resultant adduct can be further purified by passage through a conventional sizing column to remove cross-linked dextrans. An estimate of the number of available primary amino groups on the AD can be effected by reaction of a weighed sample with trinitrobenzenesulfonic acid and correlation of the optical density at 420 nm with a standard. This method normally results in essentially complete conversion of the calculated number of aldehyde groups to primary amine groups on the AD.

Alternatively, the dextran can be derivatized by conventional methods for introducing amine functions, e.g., by reaction with cyanogen bromide, followed by reaction with a diamine. The AD should be reacted with a derivative of the particular drug or chelator, in an activated form, preferably a carboxyl-activated derivative, prepared by conventional means, e.g., using dicyclohexylcarbodiimide (DCC) or a water soluble variant thereof.

It will be appreciated that the foregoing is merely illustrative of art-recognized methods for appending radioactive labels and/or drugs or toxins to antibodies/fragments and that other methods can be used to prepare conjugates according to the invention.

The scintigraphic imaging method of the invention is practiced by injecting a human patient parenterally with an effective amount for scintigraphic imaging of the radiolabeled antibody conjugate. By parenterally is meant, e.g., intravenously, intraarterially, intrathecally, interstitially or intracavitarily. It is contemplated that a subject will receive a dosage of from about 1 mCi to 50 mCi of radiolabeled conjugate, the amount being a function of the particular radioisotope and mode of administration. For intravenous injection, the amounts are normally: about 2–10 mCi, preferably about 2–5 mCi, of I-131; about 5–10 mCi, preferably about 8 mCi, of I-123; about 10–40 mCi, preferably about 20 mCi of Tc-99m; about 2–5 mCi, preferably about 4 mCi of In-111 or Ga-67. Amounts of other imaging radionuclides will be readily determined by the ordinary skilled artisan, by reference to the above isotopes and in view of the half-life of the nuclide and the size of the antibody/fragment/composite to which it is to be conjugated.

The radiolabeled antibody composite is conveniently provided as an injectable preparation for mammalian use, preferably a sterile injectable preparation for human use, for targeting a scintigraphic imaging agent to a focus of infection, preferably comprising: a sterile injectable solution containing an effective amount of the radiolabeled conjugate in a pharmaceutically acceptable sterile injection vehicle, preferably phosphate-buffered saline (PBS) at physiological pH and concentration. Other conventional pharmaceutically acceptable vehicles may be utilized as required for the site of parenteral administration.

A representative preparation to be parenterally administered in accordance with this invention will normally contain about 0.1 to 20 mg, preferably about 2 mg, of radiolabeled antibody conjugate, in a sterile solution which advantageously also contains, e.g., about 10 mg of human serum albumin (1% USP: Parke-Davis) per milliliter of 0.04M phosphate buffer (pH 7.4 Bioware) containing 0.9% sodium chloride.

Once enough isotope has deposited at the target site, scanning is effected with either a conventional planar and/or SPECT gamma camera, or by use of a hand held gamma probe used externally or internally to localize the infection. The scintigram is normally taken by a gamma imaging camera having one or more windows for detection of energies in the 50–500 KeV range. The target site can be any site having the pathogen or its antigens present in a relatively concentrated focus.

Magnetic resonance imaging (MRI) is effected in an analogous method to scintigraphic imaging except that the imaging agents will contain MRI enhancing species rather than radioisotopes. It will be appreciated that the magnetic resonance phenomenon operates on a different principle from scintigraphy. Normally, the signal generated is correlated with the relaxation times of the magnetic moments of protons in the nuclei of the hydrogen atoms of water molecules in the region to be imaged. The magnetic resonance image enhancing agent acts by increasing the rate of relaxation, thereby increasing the contrast between water molecules in the region where the imaging agent accretes and water molecules elsewhere in the body. However, the effect of the agent is to increase both $T_1$, and $T_2$, the former resulting in greater contrast, while the latter results in lesser contrast. Accordingly the phenomenon is concentration-dependent, and there is normally an optimum concentration of a paramagnetic species for maximum efficacy. The optimum concentration will vary with the particular agent used, the locus of imaging, the mode of imaging, i.e., spinecho, saturation-recovery and for various other strongly $T_1$ dependent or $T_2$ dependent imaging techniques, and the composition of the medium in which the agent is dissolved or suspended. These factors, and their relative importance are known in the art. See, e.g., Pykett, op.cit., and Runge et al., op.cit.

The MRI method of the invention is practiced by injecting a mammal, preferably a human, parenterally with an effective amount for magnetic resonance imaging of a conjugate according to the present invention of an antibody conjugate including an MRI enhancing agent. It is contemplated that a subject will receive a dosage of labeled conjugate sufficient to enhance the MRI signal at the site of infection by at least about 20%, preferably 50–500%, the amount being a function of the particular paramagnetic species and the mode of administration.

Again, the labeled antibody conjugate is conveniently provided as an injectable preparation for mammalian use, preferably a sterile injectable preparation for human use. A typical preparation for targeting a MRI agent to a focus of infection preferably comprises: a sterile injectable solution containing an effective amount of the labeled conjugate in a pharmaceutically acceptable sterile injection vehicle, preferably phosphate-buffered saline (PBS) at physiological pH and concentration. Other conventional pharmaceutically acceptable vehicles for parenteral administration may be utilized as required for the site of parenteral administration.

A representative preparation to be parenterally administered in accordance with this invention will normally contain about 0.1 to 50 mg, preferably about 5 mg, of labeled polyspecific antibody composite, in a sterile solution which advantageously also contains, e.g., about 10 mg of human serum albumin (1% USP: Parke-Davis) per milliliter of 0.04M phosphate buffer (pH 7.4 Bioware) containing 0.9% sodium chloride. Once enough of the MRI agent has deposited at the target site, scanning is effected with a conventional MRI camera to image the infection.

In a preferred embodiment of this invention, the localization ratio of the primary labeled antibody conjugate is enhanced through the use of a nonlabeled second antibody to scavenge non-targeted circulating conjugate and promote its clearance, as disclosed for related imaging agents in Goldenberg, U.S. Pat. No. 4,624,846, the disclosure of which is incorporated herein in its entirety by reference. This technique is likewise applicable to an antibody or antibody composite conjugated to a therapeutic drug, as will be discussed hereinafter. The term "localization ratio" is utilized in its conventional sense, i.e. the ratio of target to nontarget antibody conjugate. In general, the second antibody is used in an amount that will enhance the localization ratio of the primary antibody conjugate by at least about 20 percent and typically by 50 percent or more.

The second antibody may be whole IgG or IgM, or a fragment of IgG or IgM, so long as it is capable of binding the primary antibody conjugate to form a complex which is cleared from the circulation and the non-target spaces more rapidly than the primary antibody conjugate by itself.

Preferably, the second antibody will be whole IgG or IgM. If the primary antibody is a fragment of IgG or IgM, it is preferable that the second antibody be whole IgG or IgM so that the primary/secondary complex retains the capability of activating the complement cascade. Conversely, where the primary antibody is whole IgG, the second antibody may be a fragment if the complex still retains complement-fixing capability.

It is preferred that at least one of the primary/secondary pair be whole IgG or IgM. One advantage of using IgM is that it forms a higher molecular weight complex with primary antibody or with detached conjugates, ie., diagnostic and/or therapeutic principles such as drugs, chelating agents, radionuclides, and the like. This will increase the rate and effectiveness of clearance of non-target primary antibody and/or principle, especially from blood.

The second antibody can be prepared by methods disclosed in the aforementioned Goldenberg '846 patent. Monoclonal anti-species IgG is also available and is advantageously used as second antibody in the present process. Non-metallic conjugates, e.g., radioiodinated linking groups or organic paramagnetic species such as nitroxides, can also be haptens to which the second antibody is specific.

The second antibody is injected into the subject after a sufficient time has elapsed following parenteral administration of the primary polyspecific antibody conjugate to permit maximum uptake thereof by foci of infection, typically about 2–72 hours following the initial administration, preferably at about 4–48 hours post-administration. If the primary antibody is not administered intravenously, it may be advantageous to administer at least a portion of the second antibody by the same parenteral route. It is advantageous however, to inject at least a portion of the second antibody intravenously to accelerate clearance of primary antibody which has diffused into the circulatory system.

An alternative or adjunct to the use of second antibody to clear circulating labeled primary antibody and enhance the localization ratio of the primary antibody is utilization of image-enhancing subtraction techniques as disclosed in the foregoing Goldenberg patents as well as the references cited therein. This is an art-recognized technique wherein an indifferent antibody or fragment is labeled with a radionuclide capable of independent detection, and the labeled indifferent antibody is injected into the subject. This antibody has substantially the same kinetics of distribution and metabolism as the primary antibody during the period required for imaging. The injection of such antibodies is preferred over conventional subtraction agents, such as Tc-99m-labeled serum albumin, which are nevertheless suitable for use to enhance image processing by compensating for background. The use of the radiolabeled indifferent antibody as a subtraction agent permits computerized correction for nontarget background radiation from organs which effect clearance of antibodies from the circulatory system.

It will be appreciated by those of ordinary skill in the art that the primary monoclonal antibody and the indifferent antibody utilized as a subtraction agent are preferably from the same species or myeloma/hybridoma so that the second antibody will clear the primary monoclonal antibody and the indifferent antibody immunoglobulin from untargeted areas at substantially- the same rate. It is further preferred that the second antibody be specific to a constant region of the primary and indifferent immunoglobulin species.

The amount of second antibody introduced will generally be that amount which can decrease the circulating primary antibody by 10–85% within 2–72 hours. The ratio of second antibody to primary antibody which will affect the clearance will depend upon the binding properties of the primary and secondary antibody pair. Preliminary screening of patient blood in vitro can be used to provide an initial estimate of the appropriate ratio. The screen will be used to determine the ratio of second antibody to primary antibody required to obtain, a precipitin band in, e.g., a gel diffusion test. This indicates the general range of the molar ratio of second antibody to primary antibody, which serves as a measure of the lower limit for the ratio, since in vivo application may require a higher ratio of second antibody to primary antibody than is indicated by such in vitro tests.

In practice, the molar ratio of second antibody to primary antibody will generally be in the range of about 5–50, although the range should not be considered limitative. Molar ratios of second antibody to primary antibody of 15–25, and preferably 20–25, have been found to be advantageous where both the primary and the second antibody are whole IgG.

Imaging preparations and kits can include second antibody, in a separate container, for injection at an appropriate time after administration of the antibody conjugate.

Many drugs and toxins are known which have a cytotoxic effect on pathogens microbes that may infect a human. They can be found in any of the readily available art-recognized compendia of drugs and toxins, such as the Merck Index and the like. Any such antibiotic or cytotoxic drug can be conjugated to an anti-pathogen antibody or antibody composite to form a therapy agent according to the present invention, and the use of such a conjugate to improve the targeting of an antibiotic or cytotoxic drug to a focus of infection so as to increase its effective concentration at the site is a part of the present invention.

One or more antibiotic or cytotoxic drugs can be conjugated to a polymeric carrier which is then conjugated to the antibody or antibody composite, for therapeutic use. In certain cases, it is possible to partially or completely detoxify a drug as part of the antibody conjugate, while it is in circulation, which can reduce systemic side effects of the drug or toxin and permit its use when systemic administration of the drug would be unacceptable. Administration of more molecules of the drug conjugated to a polymer which is further conjugated to the antibody, permits therapy while mitigating systemic toxicity.

The methodology of this invention is applicable to the therapeutic treatment of infections by conjugating the primary antibody or antibody composite to an antibiotic or cytotoxic drug or toxin. Art-recognized methods of conjugating drugs or toxins to immunoglogulins are described, e.g., in: the chapter by O'Neill, entitled "The Use of Antibodies as Drug Carriers," in Drug Carriers in Biology and Medicine, G. Gregoriadis, ed., Academic Press London, 1979; Arnon et al., Recent Results in Cancer Res. 75: 236, 1980; and Moelton et al., Immunolog. Res. 62:47, 1982, showing art awareness. These methods are quite similar to the methods employed for coupling drugs effective against various disease-causing microorganisms, such as against bacteria, viruses, fungi and diverse parasites to antibodies developed against these microorganisms, their products or antigens associated with their lesions.

Such antibiotic or cytotoxic drugs, including, e.g., tetracyclines, chloramphenicol, piperazine, chloroquine, diaminopyridines, metroniazide, isoniazide, rifampins, streptomycins, sulfones, erythromycin, polymixins, nystatin, amphotericins, 5-fluorocytosine, 5-iodo-2'deoxyuridine, 1-adamantamine, adenine arabinoside, amanitins and azidothymidine (AZT), are preferred for coupling to appropriate specific antibodies/fragments and antibody/fragment composites. Various other potential antibiotic/cytotoxic agents for use in this invention are listed in Goodman et al., "The Pharmacological Basis of Therapeutics," Sixth Edition, A. G. Gilman et al, eds., Macmillan Publishing Co., New York, 1980, showing general art awareness. Various conditions appropriate and desirable for targeting drugs to specific target sites have been reviewed e.g. by Trouet et al., in Targeting of Drugs, G. Gregoriadis et al., eds., Plenum Press, New York and London, 1982, pp. 19–30, showing clinical knowledge of how such targeting would benefit patients suffering from infectious lesions.

The use of a second antibody, as described above in an imaging context, will increase the effectiveness of the therapeutic agent according to the invention in the same manner as for the diagnostic imaging conjugate. The effectiveness of the therapeutic agent is expressed in terms of its therapeutic index which, utilized in the conventional sense, is defined as the ratio of therapeutic effects to undesirable side effects. It is often defined in terms of a quantitative measure of efficacy vs. toxicity in a standard model system, e.g., the ratio of the median lethal dose ($LD_{50}$) to the median effective dose ($ED_{50}$). The use of second antibody as described herein produces an increase in the therapeutic index of antiviral antibody and antibody composite conjugates by clearing nontarget primary antibody and/or detached therapeutic principle. In addition to being specific to the primary monoclonal antibody as discussed above, in the instance of the therapeutic preparation, the second antibody can be specific to the therapeutic agent. It can also be specific to a carrier for the therapeutic agent.

Therapeutic preparations contemplated herein comprise monospecific anti-pathogen antibodies/fragments as defined above, conjugated to a therapeutically effective radioisotope and/or antibiotic/cytotoxic drug, in a suitable vehicle for parenteral administration. A therapeutic preparation may likewise comprise a polyspecific anti-pathogen antibody/fragment composite conjugated to a radioisotope and/or antibiotic/cytotoxic drug.

It is advantageous in certain cases to combine a drug with a radionuclide, especially where the pathogen "hides" or is somewhat inaccessible. The longer range action of radionuclides can reach hidden pathogen so long as some antigen is accessible to the conjugate. Also, radiation can cause lysis of an infected cell and expose intracellular pathogen to the antimicrobial drug component of the conjugate.

Therapeutic preparations may also include a separately packaged second antibody as described above. Suitable vehicles are well known in the art and can include, e.g., analogous sterile PBS solutions to those used for administration of diagnostic imaging agents, as discussed hereinabove.

The anti-microbial polyspecific imaging conjugates and monospecific or polyspecific therapeutic conjugates according to the invention also can be conveniently provided in a therapeutic or diagnostic kit for antibody targeting to a focus of infection. Typically, such a kit will comprise a vial containing the antibody conjugate of the present invention, either as a lyophilized preparation or in an injection vehicle. If the conjugate is to be used for scintigraphic imaging or for radioisotope therapy, it will generally be provided as a cold conjugate together with reagents and accessories for radiolabeling, in separate containers, while MRI agents and therapeutic drug/toxin conjugates will generally be supplied with a paramagnetic species or an antibiotic/cytotoxic agent already conjugated to the antibody/fragment composite or monospecific antibody/fragment. The kit may further contain a second, separately packaged, unlabeled antibody or antibody fragment specific against the antibody or fragment or the therapeutic agent, a carrier therefor, or a chelating agent for the radionuclide or paramagnetic ion.

The imaging preparations and methods of this invention are able to detect and image relatively small foci of infection and are easy and safe to use. The therapeutic reagents and methods of the invention provide a means to target sites of infection with radioisotopes and drugs to improve the therapeutic index thereof, reduce their systemic side effects and enhance their efficacy.

Radionuclide immunoconjugates are particularly effective for microbial therapy. After it has been determined that labeled antibodies are localized at infectious sites in a subject, higher doses of the labeled antibody, generally from 20 mCi to 150 mCi per dose for I-131, 5 mCi to 30 mCi per dose for Y-90, or 5 mCi to 20 mCi Re-186, each based on a 70 kg patient weight, are injected. Injection may be intravenous, intraarterial, intralymphatic, intrathecal, or intracavitary (i.e., parenterally), and may be repeated. It may be advantageous for some therapies to administer multiple, divided doses of antibody or antibody composite, thus providing higher microbial toxic doses without usually effecting a proportional increase in radiation of normal tissues.

A variety of radionuclides are useful for therapy, and they may be incorporated into the specific antibody by the labeling techniques discussed above, as well as other conventional techniques well known to the art. Preferred therapeutically effective radionuclides are astatine-211, bismuth-212, yttrium-90, rhenium-186, rhenium-188, copper-67, iodine-131, and iodine-125, although other radionuclides as well as photosensitizing agents are also suitable.

A further aspect of the present invention relates to the use of antibodies containing a significant number of boron atoms, having at least the 20% natural abundance of boron-10 isotope. The boron-containing addend may be introduced by a variety of methods, such as described in U.S. Pat. No. 4,824,659 (Hawthorne), incorporated herein in its entirety by reference. The boron-10-containing antibody can be radiolabeled according to one or more of the above procedures to produce an antibody containing both one or-more radiolabels for infection detection and/or therapy and a high content of boron-10 atoms for the absorption of thermal neutrons. Alternatively, the boron-labeled antibody can be used without the attachment of a gamma-emitting isotopes to the antibody. The infectious lesions are then irradiated with a well collimated beam of thermal neutrons, which are preferentially absorbed by boron-10 nuclei on the boron-containing addends, and the activated nucleus decays rapidly to lithium-7 and an alpha-particle. These resultant alpha-particles are toxic, and their production kills adjacent microorganisms and cells.

A particularly effective application of the methods and compositions of the present invention is the treatment of acquired immune deficiency syndrome (AIDS) and the prodromal immunodeficiency known as AIDS-related complex (ARC), due to HIV infection. While there is no cure for AIDS or ARC, drugs that block reverse transcriptase activity, which is a unique feature of the HIV retrovirus, are being investigated in AIDS patients. However, patients eventually become resistant and relapse, thus requiring other therapeutic modalities.

AIDS patients develop circulating antibodies to different HIV components, such as viral core antigens, envelope glycoprotein antigen complex, and transmembrane protein. The major reactivity in AIDS patients is directed against a possible viral envelope glycoprotein of molecular weight 41,000 (gp41). It would not have been predictable that antibodies could be useful for targeting HIV in humans, since it might have been expected that the patient's own antibodies would saturate the target sites needed for targeting of the exogenous HIV antibodies.

It is now found that exogenous monoclonal antibodies to HIV, particularly antibodies specific to certain envelope glycoprotein epitopes, have high selectivity and affinity for the virus, and in fact can be distinguished in terms of epitope specificity from the naturally occurring human HIV antibodies. Immunization of mice with HIV envelope glycoprotein antigen extracts have generated monoclonal antibodies that react with different envelope antigen epitopes. Single such monoclonals, but preferably a combination of such antibodies, are preferred antibody components of the antibody conjugate according to the invention, for use in HIV infection detection, imaging and therapy. Alternatively, human or simian antibodies can be isolated from their hosts by conventional immunoglobulin isolation and purification methods, and selected as targeting agents by their ability to target (e.g., by immunofluorescent staining methods) HIV-infected cells in vitro. Human antibodies are preferably those which target epitopes on the virus that are different and separate from major antigenic sites. Simian antibodies are preferably produced in animals in which successful models of HIV infection have been achieved. Monoclonal human or simian antibodies can be produced by known techniques, involving, e.g., transfection of mouse myeloma cells with human or simian DNA for antibody production, as disclosed, e.g., in Gillies et al., Biotechnology, 7(8):799–804, 1989; Nakatani et al., Biotechnology, 7(8):805–810.

Thus, a composite HIV antibody preparation, conjugated to a radionuclide, e.g., bismuth-212 or another short-range alpha-emitter, or to an inhibitor of reverse transcriptase, can be used at therapeutic doses of the radionuclide or drug to effectively treat patients with AIDS.

Other diseases also have proven to be resistant or refractory towards systemic chemotherapy. These include various viral, fungal, bacterial and protozoan infections, as well as particular parasitic infections. Other viral infections include those caused by influenza virus, herpes virus, e.g., Epstein-Barr virus and cytomegalovirus, rabies virus (Rhabdoviridae) and papovavirus, all of which are difficult to treat with systemic antibiotic/cytotoxic agents. Use of antibody conjugates, especially conjugates of antibody/fragment composites, to target such virus provides a significantly higher therapeutic index for antiviral drugs and toxins, thus enhancing their efficacy and reducing systemic side effects. Targeted radioimmunotherapy with conjugates of antibodies/fragments and/or composites thereof with therapeutic radioisotopes (including boron addends activatable with thermal neutrons) offers a new approach to antiviral therapy Protozoans that are relatively resistant to systemic chemotherapy include, e.g., Plasmodia (especially *P. falciparum*, the malaria parasite), *Toxoplasma gondii* (the toxoplasmosis infectious agent), Leishmaniae (infectious agent in leishmaniasis), and *Escherichia histolytica*. Detection and treatment of malaria in its various stages is significantly enhanced using the antibody/fragment conjugates of the invention. As noted above, MAbs that bind to sporozoite antigens are known. However, since sporozoite antigens are not shared by blood stage parasites, the use of MAbs against sporozoite antigens for targeting is limited to a relatively short period of time in which the sporozoites are free in the circulation, prior to and just after injection of and development in the host's hepatocytes. Thus, it is preferable to use a mixture of MAbs or a MAb composite against, e.g., more than one parasite stage of *P. falciparum*, as a targeting agent for the more effective treatment of malaria in humans that are not responding to conventional chemotherapy. The MAbs are conjugated to a suitable radionuclide for imaging (e.g., Tc-99m) or for therapy (e.g., astatine-211; rhenium-186), or with an antimalarial drug (e.g., pyrimethamine) for more selective therapy.

Toxoplasmosis is also resistant to systemic chemotherapy. It is not clear whether MAbs that bind specifically to *T. gondii*, or natural, host antibodies, can play a role in the immune response to toxoplasmosis but, as in the case of malarial parasites, appropriately targeting MAbs are effective vehicles for the delivery of therapeutic agents.

Schistosomiasis, a widely prevalent helminth infection, is initiated by free-swimming cercariae that are carried by some freshwater snails. As in the case of malaria, there are different stages of cercariae involved in the infectious process. MAbs that bind to a plurality of stages of cercariae, optionally to a plurality of epitopes on one or more thereof, and preferably in the form of a polyspecific composite, can be conjugated to an imaging or therapy agent for effective targeting and enhanced therapeutic efficacy.

MAbs that bind to one or more forms of *Trypanosoma cruzi*, the causative agent of Chagas' disease, can be made and used for detection and treatment of this microbial infection. The MAb noted above which reacts with a cell-surface glycoprotein, as well as MAbs reactive with other surface antigens on differentiation stages of the trypanosome, are suitable for directing imaging and therapeutic agents to sites of parasitic infiltration in the body.

Another very difficult infectious organism to treat by available drugs is the leprosy bacillus (*Mycobacterium leprae*). Antibodies that specifically bind to a plurality of epitopes on the surface of *M. leprae* can be made, e.g., by challenging a mouse with attenuated or fragmented *M. leprae* or its surface antigens, and these can be used, alone or in combination, to target imaging agents and/or antibiotic/cytotoxic agents to the bacillus.

Helminthic parasitic infections, e.g., Strongyloidosis and Trichinosis, themselves relatively refractory towards chemotherapeutic agents, are suitable candidates for antibody-targeted diagnosis and therapy according to the invention, using antibodies that bind specifically to one or, preferably, to a plurality of epitopes on the parasites.

Antibodies are available or can easily be raised that specifically bind to most of the microbes and parasites responsible for the majority of infections in humans, as illustrated by the foregoing disclosure and citation of references. Many of these have been used previously for in vitro diagnostic purposes and the present invention shows their utility as components of antibody conjugates to target diagnostic and therapeutic agents to sites of infection. Microbial pathogens and invertebrate parasites of humans and mammals are organisms with complex life cycles having a diversity of antigens expressed at various stages thereof. Therefore, targeted treatment canbest be effected when antibody conjugates which recognize antigen determinants on the different forms are used in combination, either as mixtures or as polyspecific conjugates, linked to the appropriate therapeutic modality. The same principle applies to using the MAb reagents for detecting sites of infection by attachment of imaging agents, e.g., radionuclides and/or MRI enhancing agents.

To the extent that the therapeutic radioisotopes, drugs, toxins and other cytotoxic agents produce hematopoietic toxicity as a side effect of their administration, administration of an effective amount of a cytokine, especially a lymphokine or other growth factor, to mitigate or prevent such toxicity and to stimulate marrow production, is advantageous and is a part of the invention. Such administration will be effected analogously to that disclosed in commonly assigned and copending U.S. patent application Ser. No. 174,490, the entire disclosure of which is incorporated herein by reference.

Without further elaboration, it is believed that one skilled in the art can, using the preceding description, utilize the present invention to its fullest extent. The following preferred specific embodiments are therefore to be construed as merely illustrative, and not limitative of the remainder of the disclosure in any way whatsoever.

EXAMPLES

In the following examples, all temperatures are set forth uncorrect in degrees Celsius. UnLess otherwise indicated, all parts and percentages are by weight.

Example 1
Specific Murine Monoclonal Antibody to HIV-qp160

Mice are hyperimmunized with the gp160 envelope precursor-protein of HIV-1. Spleen lymphocytes from the hyperimmunized animals are fused with SP2/0 myeloma cells and the fused cells diluted in HAT in microtiter plate wells. After 10 days the supernatant from wells containing growing hybrids are tested by ELISA for reactivity with gp160. Wells containing monoclonal antibodies reactive with gp160 are subsequently screened for reactivity with HIV-1 envelope proteins gp120 and gp41 (gp160 products). Clones specific for gp160 which are not blocked by antibodies in human serum from seropositive AIDS patients, are subcloned. Four clones with high specificity and affinity, at least two of which can bind to HIV in the presence of one another (hereinafter, collectively MAb-160s, and individually MAb-160s1, MAb-160s2, MAb-160s3, MAb-160s4), are each expanded in culture, and used to produce ascites fluid in Balb-c mice. Each MAb-160s is purified from the ascites fluid by affinity chromatography on protein A. The clones are determined to be of $IgG_1$ subclass and are used to prepare conjugates.

Monoclonal antibodies to other HIV-anticens can be used in patients that do not have significant blood levels of the antigen or significant blood levels of antibody that block binding of the anti-HIV monoclonal antibody.

Example 2
Preparation of 99m-Tc-MAb-160s1-FAb' Imaging Agent

Purified MAb-160s1, prepared according to Example 1, is converted to the F(ab')$_2$ fragment with pepsin and the divalent fragment converted to Fab' by reduction with cystine. After removal of cystine by gel filtration, the Fab' is compounded with a buffered reducing agent, preferably SnCl$_2$, and lyophilized. 99m-Tc-MAb-160s1-Fab' is prepared just prior to patient injection by adding 20 mCi of 99mTc-pertechnetate in sterile saline to the vial containing the lyophilized MAb-160s1-Fab'.

Example 3
Preparation of 131-I-MAb-160s1+2-F(ab')$_2$

Purified MAb-160s1 and MAb-160s2, prepared according to Example 1, are each converted to Fab' fragments as described in Example 2. The thiol groups of the MAb-160s2 fragments are capped with iodoacetamide and the capped fragment is derivatized with maleimide-hydroxysuccinimide p-nitrobenzoate ester, and the fragments are separately purified by gel filtration. The purified fragments are reacted with one another to form a chemically linked bivalent composite with dual specificity for the gp-160 antigen. The composite is radioiodinated with I-131 by the chloramine-T method, to achieve an activity of 180 mCi per dose.

Example 4
Diagnostic Imaging

A 24 year old male patient is being treated with AZT and becomes resistant to the drug, expressing HIV-p24 antigen in his blood. He exhibits malaise and has daily -episodes of chills and fever. An immunoscintigraphy study is performed using an imaging agent prepared according to Example 2. To the vial containing 1 mg of lyophilized Fab' is added 20 mCi of generator-produced sodium pertechnetate in PBS. After 5 minutes, the imaging agent is injected and the patient is scanned 3 hours later with a gamma camera in SPECT/ mode. Intense foci of bound Tc-99m are observed in numerous lymph nodes and in the spleen.

Analogous detection and imaging of other viral infections can be effected using single antibody or multiple antibody radiolabeled or MRI enhancer-labeled conjugates, according to the general methods illustrated in the foregoing examples.

Example 5
AIDS Therapy

The patient of Example 4 is given a 5 mCi dosimetry injection of 131-I-MAb-160s1+2-F(ab')$_2$, prepared from an aliquot of a standard dose according to Example 3. Planar imaging using a gamma camera shows intense accumulation of I-131 in the same sites imaged with 99m-Tc-MAb-160s-Fab'. Blood pharmacokinetics indicate that the patient can be safely treated with 180 mCi of the radioiodinated MAb. He is injected with 180 mCi of 131-I-MAb-160s-1+2-F(ab')$_2$. Over the course of the next two weeks, blood levels of p24-HIV antigen drop rapidly and antigen is undetectable after 3 weeks. A second imaging study after four weeks with 99m-Tc-MAb-160s-Fab' is negative, failing to show localization of bound Tc-99m in lymph nodes or spleen. At this time, the patient shows other signs of improvement, with abatement of fever.

Analogous anti-viral therapeutic conjugates can be made for treatment of other viral infections, using the general methodology illustrated in the foregoing examples.

Example 6
Anti-malarial Antibodies

Mice are hyperimmunized with merozoites from *Plasmodium falciparum*. Spleenocytes from the hyperimmunized animals are fused with SP2/0 myeloma cells and the fused cells diluted in HAT in microtiter late wells. After 10 days, the supernatant from ells containing growing hybrids are tested for specific binding to merozoites bound to polyacrylamide beads with glutaraldehyde, using an I-125-labeled rabbit anti-mouse IgG. Hybridoma clones from wells containing merozoite-binding monoclonal antibodies are subcloned. Three of the 20 positive clones, each of which can bind to merozoites in 1e presence of one another (hereinafter, collectively α-mer-MAb, and individually α-mer-MAb1, , α-mer-MAb2 and α-mer-MAb3), are each expanded in culture, and used to produce ascites fluid in Balb-c mice. Each α-mer-MAb is purified from the ascites fluid by affinity chromatography on protein A. The clones are determined to be of IgG$_1$ subclass and are used to prepare conjugates.

By a completely analogous route, three clones that bind specifically to *P. falciparum* sporozoites (hereinafter, collectively α-spo-MAb, and individually α-spo-MAb1, α-spo-MAb2 and α-spo-MAb3) are made, expanded and ascites-produced monoclonals are purified. They are also determined to be of the IgG$_1$ subclass.

Example 7
Preparation of Anti-malarial Conjugate

Each of the purified α-mer-MAbs and α-spo-MAbs prepared according to Example 6 is converted to a Fab' fragment with pepsin, followed by cystine reduction, analogously to the procedure of Example 2, and the fragments are capped with excess iodoacetamide. To an equimolar mixture of the six different capped Fab' fragments, in aqueous solution, at pH 4.5, is added a 50-fold molar excess of glutaraldehyde, followed about 5–15 minutes later by a 30-fold molar excess of pyrimethamine (each relative to the total number of moles of antibody fragments), and the mixture is incubated for 6 hr at 37° C. The resultant conjugate has an average of 2–3 Fab' fragments and 5–10 pyrimethamines per conjugate molecule. The conjugate is freed of low molecular weight reagents on a short polyacrylamide gel column and sterile filtered.

Example 8
Malaria Therapy

A patient suffering from a late stage attack of *P. falciparum* malaria and experiencing chills and fever is infused with a solution of the anti-malarial conjugate according to Example 7, in physiological saline. A rapid drop in blood levels of merozoites is observed and the chills and fever subside within a few hours. The patient's liver receives both merozoite-conjugate complexes and uncomplexed conjugate, both of which release pyrimethamine to sporozoites, thereby inhibiting recurrence of the attack. In addition, slow hydrolytic cleavage of the Schiff base linkages to pyrimethamine producers a prolonged plasma level of the drug which also effects a suppressive cure of the infection. Frequent monitoring of the patient's blood permits the infusion to be adjusted to achieve optimal drug levels and therapeutic effect.

Analogous conjugates using single or multiple antibody/ fragment conjugates of drugs or radionuclides that bind to toxoplasmosis protozoan antigens, schistosomal antigens, trypanosomal antigens, bacterial, fungal and other microbial or parasitic antigens can be produced by variation of the foregoing illustrative methods in ways that the skilled artisan will appreciate, and the infections caused by such pathogens can be treated using these conjugates.

Example 9
Specific Monoclonals to *Mycobacterium leprae*

A series of monoclonal antibodies that specifically bind to leprosy bacilli are produced by hyperimmunization of mice with a sonicate of *Mycobacterium leprae*, fusion of resultant splenocytes and screening of clones for specific binding to the bacilli by conjugating supernatant from wells containing growing hybrids with fluorescein, incubating the conjugates with fixed *M. leprae*, washing, and detecting bound antibodies under u.v. light. Four positive clones are subcloned, expanded and ascites-produced antibodies are purified according to procedures analogous to those of Example 1.

Example 10
Preparation of Leprosy Therapeutic Conjugate

A mixture of the four monoclonal antibodies produced according to Example 9 is gently oxidized with periodate to cleave an average of one sugar residue in the carbohydrate region. An aminodextran to which an average of twenty carboranes are attached is reacted with the oxidized antibody, and the Schiff base conjugate is stabilized with borohydride. The resultant conjugate is radioiodinated with I-131, analogously to the procdure of Example 3, to achieive an activity of 70 mCi per dose.

Example 11

Leprosy Therapy

A patient suffering from acute, disseminated leprosy, with high fever and numerous skin lesions, that has been refractory to conventional chemotherapy, is infused intravenously with a 70 mCi dose in saline of the conjugate produced according to Example 10. Gradual reduction in fever occurs, with localization of the conjugate at the sites of subcutaneous lesions and in other foci, which are detectable by gamma scintigraphy. After five days, non-localized conjugate is substantially cleared and excreted, but lesions and foci of infection still contain bound conjugate. The patient is then exposed to a collimated thermal neutron beam, focussed on the scintigraphically detected lesions and foci of infection. Within the following week, significant necrosis at the site of the lesions is observed, and regeneration of tissue commences at the borders of the lesions. Conventional chemotherapy is then resumed, with further improvement shown, permitting eventual successful management of the patient.

The preceding examples can be repeated with similar success by substituting other described reactants and/or operating conditions of this invention for those used in the preceding examples. Thus, antibodies to other human disease-producing pathogens and/or their antigens, e.g., any of the other illustrative pathogens enumerated herein, can be produced and incorporated into imaging and therapy agents according to the invention, and can achieve successful diagnostic and therapeutic results in patients.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A method of targeting a therapeutic agent to a focus of infection, which comprises parenterally injecting a patient infected with a pathogen with an effective amount of a polyspecific antibody-therapeutic agent conjugate;
   wherein said conjugate comprises an immunoreactive composite of a plurality of chemically-linked antibodies or antibody fragments which specifically binds to a plurality of accessible epitopes on a single species of pathogen or of an antigen shed by said pathogen or resulting from the fragmentation or destruction of said pathogen and which is accreted at said focus of infection,
   wherein said polyspecific antibody conjugate further comprises a chemically bound therapeutic agent for treating said infection.

2. The method of claim 1, wherein said agent is a therapeutic radioisotope or boron addend.

3. The method of claim 1, wherein said agent is an anti-pathogenic drug or cytotoxic agent.

4. The method of claim 1, wherein said accessible epitopes are not saturated or blocked by the patient's native antibodies.

5. The method of claim 4, wherein said polyspecific antibody conjugate comprises chemically-linked monoclonal antibodies or antigen-binding fragments thereof.

6. The method of claim 1, wherein said polyspecific antibody conjugate is a conjugate of an antiserum or is a conjugate of antibody fragments of an antiserum which specifically bind a plurality of epitopes on a single species of pathogen.

7. The method of claim 6, wherein said antiserum is affinity purified by removal of antibodies which bind to antigens associated with said pathogen circulating at a significant level in the patient's bloodstream.

8. The method of claim 6, wherein said antiserum is affinity purified by contact with bound pathogen or pathogen-associated antigens, and subsequent recovery of antiserum enriched in antibodies that bind to said pathogen or pathogen-associated antigens.

9. The method of claim 1, wherein said pathogen is a protozoan.

10. The method of claim 9, wherein said protozoan is selected from the group consisting of *Plasmodium falciparum, Plasmodium vivax, Toxoplasma gondii, Trypanosoma rangeli, Trypanosoma cruzi, Trypanosoma rhodesiensei, Trypanosoma brucei, Schistosoma mansoni, Schistosoma japanicum, Babesia bovis, Elmeria tenella, Onchocerca volvulus, Leishmania tropica, Trichinella spiralis, Onchocerca volvulus, Theileria parva, Taenia hydatigena, Taenia ovis, Taenia saginata, Echinococcus granulosus* and *Mesocestoides corti*.

11. The method of claim 1, which further comprises administering to said patient, at a time after administration of said conjugate sufficient to optimize uptake of said conjugate at the site of said infection, an amount of a second antibody that specifically binds to said conjugate sufficient to reduce the amount of said conjugate in circulation by 10–85% within 2–72 hours.

12. The method of claim 1, wherein said agent is a therapeutic antibiotic or cytotoxic agent that causes hematopoietic toxicity as a side effect of its administration, and wherein said method further comprises administering to said patient, at a ltime prior to, concomitant with or subsequent to administration of said therapeutic conjugate, an amount of a cytokine sufficient to mitigate or prevent the hematopoietic toxicity of said agent.

13. The method of claim 1, wherein said pathogen is a microbial pathogen or an invertebrate parasite that expresses a diversity of antigens at various stages of its life cycle, and wherein said imunoreactive composite comprises antibodies or antibody fragments which bind to antigens expressed at different stages of the life cycle of said pathogen or said parasite.

14. The method of claim 13, wherein said th erapeutic agent is sel ected from the group consisting of a therapeutic radioisotope, a boron addend, an anti-pathogenic drug and a cytotoxic agent.

15. The method of claim 13, wherein said epitopes are not saturated or blocked by the patient's native antibodies.

16. The method of claim 13, wherein said polyspecific antibody conjugate comprises chemically-linked monoclonal antibodies or antigen-binding fragments thereof.

17. The method of claim 13, wherein said polyspecific antibody conjugate is a conjugate of an antiserum or is a conjugate of antibody fragments of an antiserum which specifically bind a plurality of epitopes on a single species of pathogen.

18. The method of claim 17, wherein said antiserum is affinity purified by the removal of antibodies which bind to antigens associated with said pathogen circulating at a significant level in the patient's bloodstream; and/or by contact with bound pathogen or pathogen-associated antigens, and subsequent recovery of antiserum enriched in antibodies that bind to said pathogen or pathogen-associated antigens.

19. The method of claims 13, wherein said pathogen is a protozoan selected from the group consisting of *Plasmodium falciparum, Plasmodium vivax, Toxoplasma gondii, Txypanosoma rangeli, Trypanosoma cruzi, Trypanosoma rhodesiensei, Trypanosoma brucei, Schistosoma mansoni, Schistosoma japanicum, Babesia bovis, Elmeria tenella, Onchocerca volvulus, Leishmania tropica, Trichinella spiralis, Theileria parva, Taenia hydatigena, Taenia ovis, Taenia saginata, Echinococcus granulosus* and *Mesocestoides corti*.

20. The method of claim 13, wherein said pathogen is a helminth or a malarial parasite.

21. The method of claim 13, wherein said therapeutic agent is an antibiotic or cytotoxic agent that causes hematopoietic toxicity as a side effect of its administration, and wherein said method further comprises the step of administering to said patient at a time prior to, concomitant with or subsequent to the administration of said therapeutic conjugate, an amount of a cytokine sufficient to mitigate or prevent the hematopoietic toxicity of said agent.

22. The method of claim 1, wherein said pathogen is a virus.

23. The method of claim 22, wherein said virus is an RNA virus.

24. The method of claim 22, wherein said virus is a DNA virus.

25. The method of claim 22, wherein said virus is selected from the group consisting of the human immunodeficiency virus (HIV), herpes virus, cytomegalovirus, rabies virus, influenza virus, hepatitis B virus, Sendai virus, feline leukemia virus, Reo virus, polio virus, human serum parvo-like virus, simian virus 40, respiratory syncytial virus, mouse mammary tumor virus, Varicella-Zoster virus, Dengue virus, rubella virus, measles virus, adenovirus, human T-cell leukemia viruses, Epstein-Barr virus, murine leukemia virus, mumps virus, vesicular stomatitis virus, Sindbis virus, lymphocytic choriomeningitis virus, wart virus, and blue tongue virus.

26. The method of claim 1, wherein said pathogen is bacterium.

27. The method of claim 26, wherein said bacterium is selected from the group consisting of Streptococcus agalactiae, Legionella pneumophilia, Streptococcus pyogenes, Escherichia coli, Neisseria gonorrhosae, Neisseria meningitidis, Pneumococcus, Hemophilus influenzae B, Treponema pallidum, Lyme disease spirochetes, Pseudomonas aeroginosa, Mycobacterium leprae, Brucella abortus, Mycobacterium tuberculosis, and Tetanus toxin.

28. The method of claim 1, wherein pathogen is a helminth.

29. The method of claim 1, wherein said pathogen is mycoplasma.

30. The method of claim 29, wherein said mycoplasma is selected from the group consisting of Mycoplasma arthritidis, M. hyorhinis, M. orale, M. arginini, Acholeplasma laidlawii, M. salivarum, and M. pneumoniae.

31. The method of claim 1, wherein said pathogen is a fungus.

* * * * *